US007166447B2

(12) United States Patent
Umezawa et al.

(10) Patent No.: US 7,166,447 B2
(45) Date of Patent: Jan. 23, 2007

(54) PROBE FOR ANALYZING PROTEIN—PROTEIN INTERACTION AND METHOD OF ANALYZING PROTEIN—PROTEIN INTERACTIONS WITH THE USE OF THE SAME

(75) Inventors: Yoshio Umezawa, Tokyo (JP); Takeaki Ozawa, Chiba (JP)

(73) Assignee: Japan Science and Technology Corporation, Saitama (JP)

( * ) Notice: Subject to any disclaimer, the term of this patent is extended or adjusted under 35 U.S.C. 154(b) by 496 days.

(21) Appl. No.: 10/089,040

(22) PCT Filed: Dec. 27, 2000

(86) PCT No.: PCT/JP00/09348

§ 371 (c)(1),
(2), (4) Date: Apr. 16, 2002

(87) PCT Pub. No.: WO02/08766

PCT Pub. Date: Jan. 31, 2002

(65) Prior Publication Data

US 2003/0003506 A1 Jan. 2, 2003

(30) Foreign Application Priority Data

Jul. 26, 2000 (JP) ............................. 2000-224939

(51) Int. Cl.
*C12N 15/52* (2006.01)
*C12N 15/62* (2006.01)
*C12N 15/79* (2006.01)
*C12N 9/02* (2006.01)
*C12Q 1/26* (2006.01)

(52) U.S. Cl. ..................... 435/69.7; 435/4; 435/7.6; 435/8; 435/252.3; 435/320.1; 536/23.2; 536/23.4

(58) Field of Classification Search ............... 435/69.7, 435/6, 252.3
See application file for complete search history.

(56) References Cited

U.S. PATENT DOCUMENTS 5,795,731 A 8/1998 Belfort ..................... 435/32

(Continued)

FOREIGN PATENT DOCUMENTS

WO 00/18881 4/2000

(Continued)

OTHER PUBLICATIONS

Chong, Shaorong, et al., Sep. 6, 1996, "Protein splicing involving the *Saccharomyces cerevisiae* VMA intein", The Journal of Biological Chemistry, vol. 271, No. 36, pp. 22159-22168.*

(Continued)

*Primary Examiner*—Nashaat T. Nashed
*Assistant Examiner*—William W. Moore
(74) *Attorney, Agent, or Firm*—Wenderoth, Lind & Ponack, L.L.P.

(57) ABSTRACT

A probe for protein—protein interaction analysis suitable for analyzing protein—protein interactions of various proteins with high accuracy and in a simple manner and a method for analyzing interaction of two proteins by using the probe. With the probe, protein splicing is caused by protein—protein interaction, and a physicochemically or biochemically detectable protein is regenerated.

8 Claims, 11 Drawing Sheets

U.S. PATENT DOCUMENTS

| | | | | |
|---|---|---|---|---|
| 5,834,247 | A | * | 11/1998 | Comb et al. ............... 435/69.7 |
| 5,998,136 | A | * | 12/1999 | Kamb ........................... 435/6 |
| 6,544,786 | B1 | * | 4/2003 | Xiao et al. ................. 435/325 |
| 6,551,786 | B1 | * | 4/2003 | Manfredi ....................... 435/6 |
| 6,562,576 | B1 | * | 5/2003 | Manfredi ....................... 435/6 |
| 6,770,446 | B1 | * | 8/2004 | Young et al. ................ 435/7.1 |
| 6,824,981 | B1 | * | 11/2004 | Chait et al. .................... 435/6 |
| 6,858,775 | B1 | * | 2/2005 | Xu et al. .................... 800/278 |
| 2002/0106632 | A1 | * | 8/2002 | Manfredi ....................... 435/4 |
| 2002/0106693 | A1 | * | 8/2002 | Manfredi ................... 435/7.1 |
| 2002/0106698 | A1 | * | 8/2002 | Manfredi ................... 435/7.3 |
| 2002/0106699 | A1 | * | 8/2002 | Manfredi et al. ............ 435/7.3 |
| 2002/0151006 | A1 | * | 10/2002 | Muir et al. ................. 435/183 |
| 2002/0177691 | A1 | * | 11/2002 | Scott et al. ................. 530/350 |
| 2003/0003439 | A1 | * | 1/2003 | Ostanin ......................... 435/4 |
| 2003/0013148 | A1 | * | 1/2003 | Evans et al. .............. 435/68.1 |
| 2003/0167533 | A1 | * | 9/2003 | Yadav et al. ............... 800/288 |

FOREIGN PATENT DOCUMENTS

| WO | 00/34514 | 6/2000 |
|---|---|---|
| WO | 00/36093 | 6/2000 |

OTHER PUBLICATIONS

Wu, Hong, et al., 1998, "Protein trans-splicing and functional mini-inteins of a cyanobacterial dnaB intein", Biochimica et Biophysica Acta, vol. 1387, pp. 422-432.*

Shingledecker, Kaori, et al., 1998, "Molecular dissection of the *Mycobacterium tuberculosis* RecA intein: design of a minimal intein and of a trans-splicing system involving two intein fragments", Gene, vol. 207, pp. 187-195.*

Karimova, Gouzel, et al., May 1998, "A bacterial two-hybrid system based on a reconstituted signal transduction pathway", Proceedings of the National Academy of Sciences, USA, vol. 95, pp. 5752-5756.*

Waud, Jonathan P., et al., 1996, "Engineering the C- terminus of firefly luciferase as an indicatof of covalent modification of proteins", Biochimica et Biophysica Acta, vol. 1292, pp. 89-98.*

Wu, Hong et al., Aug. 1998, "Protein trans-splicing by a split intein encoded in a split dnaE gene of *Synechocystis* sp. PCC6803", Proceedings of the National Academy of Sciences, USA, vol. 95, pp. 9226-9231.*

Lew, Belinda M., et al., 1999, "Characteristics of protein splicing in trans mediated by a semisynthetic split intein", Biopolymers, vol. 51, pp. 355-362.*

Conti, Elena, et al., Mar. 1996, "Crystal structure of firefly luciferase throws light on a superfamily of adenylate-forming enzymes", Structure, vol. 4, pp. 287-298.*

Evans, Thomas C., Jr., et al., Feb. 12, 1999, "The in vitro ligation of bacterially expressed proteins using an intein from *Methanobacterium thermoautotrophicum*", The Journal of Biological Chemistry, vol. 274, No. 7, pp. 3923-3926.*

Remy, Ingrid, et al., May 1999, "Clonal selection and in vivo quantitation of protein interactions with protein-fragment completion assays", Proceedings of the National Academy of Sciences, USA, vol. 96, pp. 5394-5399.*

Amitai, Gil, et al., Sep. 1999, "Fine-tuning an engineered intein", Nature Biotechnology, vol. 17, pp. 854-855.*

Evans, Thomas C., Jr., et al., Mar. 31, 2000, "Protein trans-splicing and cyclization by a naturally split intein from the dnaE gene of *Synechocystis* species PCC6803", The Journal of Biological Chemistry, vol. 275, No. 13, pp. 9091-9094.*

Chong, Shaorong, et al., Jun. 20, 1997, "Protein splicing of the *Saccharomyces cerevisiae* VMA intein without the endonuclease motifs", The Journal of Biological Chemistry, vol. 272, No. 25, pp. 15587-15590.*

M. J. Closton et al., "The ins and outs of protein splicing elements", Molecular Microbiology, vol. 12, No. 3, pp. 359-363, 1994.

* cited by examiner

FIG. 2

```
VDE --------⁴⁵⁰V V V H N C⁴⁵⁵
EGFP --------I E L K G I--------
             124          129 m125 : E125I, I129C            I I L K G C
m126 : E125I, L126Y, I129C     I I Y K G C
m129 : I129C                   I E L K G C
```

F I G. 3
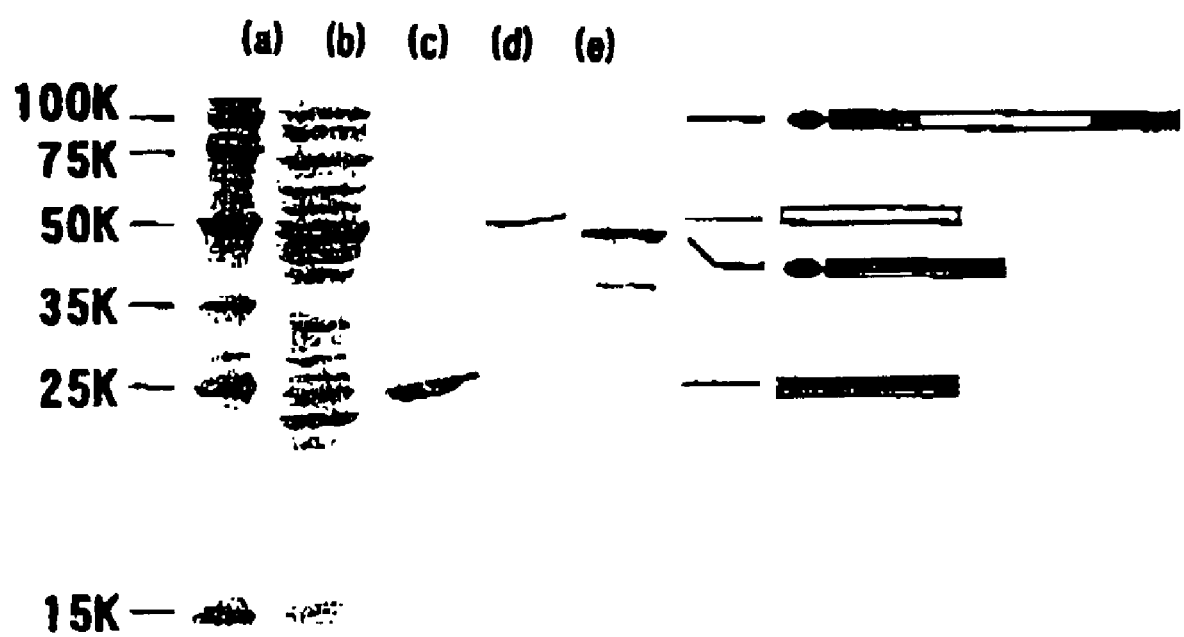

FIG. 5

A (a) (b) (c) (d) (e) (f)
—— His-NE-NV-(linker)-CaM
—— His-NE-NV-(linker)-M13
—— His-NE-NV-(linker)

B (a) (b) (c) (d) (e) (f)
—— CaM-(linker)-CV-CE
—— M13-(linker)-CV-CE
—— (linker)-CV-CE

PROBE FOR ANALYZING PROTEIN—PROTEIN INTERACTION AND METHOD OF ANALYZING PROTEIN—PROTEIN INTERACTIONS WITH THE USE OF THE SAME

This application is a 371 of PCT/JP00/009348, filed Dec. 27, 2000.

TECHNICAL FIELD

The invention of this application relates to a probe for protein—protein interaction analysis, and to a method for the analysis of protein—protein interactions using such a probe. More specifically, the invention of this application relates to a probe for protein—protein interaction analysis and to a method for the analysis of protein—protein interactions using such a probe, which enable accurate and simple analysis of protein—protein interactions in all living cells.

BACKGROUND ART

Protein—protein interactions are known to play an important role with respect to structure and functions of living cells.

Many problems currently studied in molecular biology and biochemistry, such as gene transcription mechanism and intracellular information signaling, are related to protein—protein interactions.

Some of the problems in the field of molecular biology and biochemistry have been heretofore solved by the development of a two-hybrid method (Chien, C. T., Bartel, P. L., Sternglanz, R., Fields, S., *Proc. Natl. Acad. Sci.* USA 1991, 88, 9578–9582; Fields, S., Song, O., *Nature* 1989, 340, 245–246) by which screening is conducted based on interaction of a "bait" protein and a "prey" protein in a protein library. The two-hybrid method has been suggested as an effective method that facilitates the identification of candidate molecules for protein—protein interaction and also creates new protein—protein interaction maps (Flores, A., Briand, J. F., Gadal, O., Andrau, J. C., Rubbi, L., Mullem, V., Boschiero, C., Goussot, M., Marck, C., Carles, C., Thuriaus, P., Sentenac, A., Werner, M., *Proc. Natl. Acad. Sci. USA* 1999, 96, 7815–7820; Ito, T., Tashiro, K., Muta, S., Ozawa, R., Chiba, T., Nishizawa, M., Yamamoto, K., Kuhara, S., Sakaki, Y., *Proc. Natl. Acad. Sci. USA* 1999, 97, 1143–1147; Walhout, A. J. M., Sordella, R., Lu, X., Hartley, J. L., Temple, G. F., Brasch, M. A., Thierry-Mieg, N., Vidal, M., *Science* 2000, 287, 116–122). However, the problem associated with the two-hybrid method is that it is applicable only to the analyzable protein interactions that occur close to the reporter gene in cell nuclei and, therefore, this method lacks generality.

Reliability is yet another problem associated with the two-hybrid method, and a confirmation test using proteins with known functions has to be conducted by employing model cells or animals for every assay (Walhout, A. J. M., et al., *Science* 1999, 287, 116–122).

Accordingly, novel methods for protein—protein interaction analysis have been suggested, those methods including a ubiquitin split protein sensor (USPS) method by which N- and C-terminal ubiquitins through reactions with proteins and a nuclear-localized reporter is activated by cleavage of a transcription factor (Dunnwald, M., Varshavsky, A., Johnsson, N., *Mol. Biol. Cell* 1999, 10, 329–344; Johnsson, N., Varshavsky, A., *Proc. Natl. Acad. Sci. USA* 1998, 95, 5187–5192; Stagljar, I., Korostensky, C., Johnsson, N., Heesen, S., *Proc. Natl. Acad. Sci. USA* 1998, 95, 5187–5192; and an SOS recruit system, in which a catalyst domain is brought close to a membrane localization domain through protein—protein interaction, a guanine exchange factor (GEF) or Ras is reconstructed, and it further complements yeast temperature-sensitive mutated yeast GEF (Aronheim, A., *Nucleic Acids Res.* 1997, 25, 3373–3374; Aronheim, A., Zandi, E., Hennemann, H., Elledge, S. J., Karin, M., *Mol. Cell. Biol.* 1997, 17, 3094–3102; Broder, Y. C., Katz, S., Aronheim, A., *Curr. Biol.* 1998, 8, 1121–1124).

As a more general approach, a split enzyme technology method has been reported (Rossi, F., Charlton, C. A. and Blau, H. M., *Proc. Natl. Acad. Sci. USA* 1997, 94, 8405–8410; Remy, I., Michnick, S. W., *Proc. Natl. Acad. Sci. USA* 1999, 96, 5394–5399; Pelletier, J. N., Arndt, K. M., Pluckthun, A., Michnick, S. W., *Nature Biotech.* 1999, 17, 683–690). With this method, a split enzyme is reconstructed through protein—protein interaction and its enzymatic activity is restored. The activity of the reconstructed enzyme can be measured by fungi or cellular phenotype or by a fluorescent enzyme substrate analogues.

These methods have a comparatively high accuracy and attain the object of assaying interactions between intracellular proteins or membrane proteins, but they are applicable to only appropriately designed cells. Another problem is that sufficient accuracy and sensitivity cannot be obtained. Still another problem is that such methods require a variety of substrates to conduct the analysis and are therefore troublesome.

Therefore, a general method or probe suitable for accurate and simple analysis of protein—protein interactions and applicable to any protein has not yet been developed.

With the foregoing in view, it is an object of the invention of the present application to solve the problems of the prior art and to provide a probe for protein—protein interaction analysis, which enables highly accurate and simple analysis of protein—protein interactions, and to a method for the analysis of protein—protein interactions using such a probe.

SUMMARY OF THE INVENTION

In order to solve the above-mentioned problems, the invention of this application firstly provides a probe for protein—protein interaction analysis, this probe serving to analyze the interaction between two proteins, wherein protein splicing is induced by protein—protein interaction and a physicochemically or biochemically detectable protein is regenerated.

Secondly, the invention provides the probe for protein—protein interaction analysis, comprising two probes: a probe "a" which comprises an N-terminal polypeptide of an intein and an N-terminal polypeptide of a labeled protein, and a probe "b" which comprises a C-terminal polypeptide of the intein and a C-terminal polypeptide of the labeled protein.

Thirdly, the invention provides the probe for protein—protein interaction analysis, wherein the C-terminal of probe "a" and the N-terminal of probe "b" each has a linker sequence.

Fourthly, the present invention provides the probe for protein—protein interaction analysis, wherein the intein is an endonuclease derived from yeast VMA; and fifthly, the invention provides the probe for protein—protein interaction analysis, wherein the intein is DnaE derived from cyanobacterium.

Sixthly, the invention provides the probe for protein—protein interaction analysis, wherein the indicator protein (e.g., labeled protein) is a fluorescent protein; and seventhly, the invention provides the probe for protein—protein interaction analysis, wherein the fluorescent protein is a green fluorescent protein (GFP).

Eighthly, the invention provides the probe for protein—protein interaction analysis, wherein the indicator protein is an emission-catalyzing enzyme; and ninthly, the invention provides the probe for protein—protein interaction analysis, wherein the emission-catalyzing enzyme is a luciferase.

Tenthly, the invention provides a method for the analysis of protein—protein interactions, comprising the steps of causing a protein linked to the probe "a" of any of the above-described second to ninth claims to be co-present with a protein linked to the probe "b" of any of the above-described second to ninth claims, and detecting a signal of the labeled protein.

Eleventhly, the invention provides the method of protein—protein interaction analysis, wherein the protein linked to the probe "a" is caused to be co-present with the protein linked to the probe "b" by introducing a polynucleotide that expresses the probe for protein—protein interaction analysis of any of the above-described first to ninth claims into an eukaryotic cell.

BRIEF DESCRIPTION OF THE DRAWINGS

FIG. 2 shows amino acid residues substituted between I124 and I129 with respect to the structure of the N-terminal polypeptide of EGFP in the Example of the present invention.

FIG. 3 shows the results of SDS-PAGE analysis of proteins expressed in E. coli and transformed with pGEX-NVC. Here, lanes (a) to (c) are Coomassie Blue-stained SDS-PAGE; lane (a) indicates the protein molecular mass standard (Novagen) with the molecular mass thereof (kDa); lane (b) indicates the crude product before a GST-affinity column; and lane (c) indicates the sample purified by the GST-affinity column. Lanes (d) and (e) show Western blotting analysis of a crude lysate; (d) shows the analysis results obtained with the antibodies specific to VDE and (e) shows the results of analysis obtained with the antibodies specific to GFP (e).

FIG. 5 shows the splicing results obtained with interaction of protein CaM and protein M13 in the Example of the present invention. Here, (a) indicates pET_NVCΔSD (C/M) (SDS-PAGE); (b) indicates pET_NVCΔSD (M/C); (c) indicates pET_NVCΔSD (/) gene 1; (d) indicates pET_NVCΔSD linker (C/M); (e) indicated pET_NVCΔSD linker (M/C); and (f) indicates pET_NVCΔSD linker (/). (A) shows the results of Western blotting obtained with anti-His labeling, and (B) shows the results of Western blotting obtained with anti-GFP labeling.

DETAILED DESCRIPTION OF THE INVENTION

The probe for protein—protein interaction analysis of the present invention is based on the principle that the interaction of two proteins, each being linked to a probe, induces splicing, the sites of split labeled proteins contained in the probes are linked and regenerate the labeled proteins, and a signal is emitted.

Protein splicing is a process wherein the internal protein segment (intein) is excised from a translated protein. In this process, the excision of intein is accompanied by the ligation of flanking sequences (exteins) (Gimble, F. S., Sci. Biol. 1998, 5, R251–256).

With the probe for protein—protein interaction analysis of the present invention, protein—protein interaction analysis is conducted by ingeniously applying such self-excision of inteins.

Figure 1:
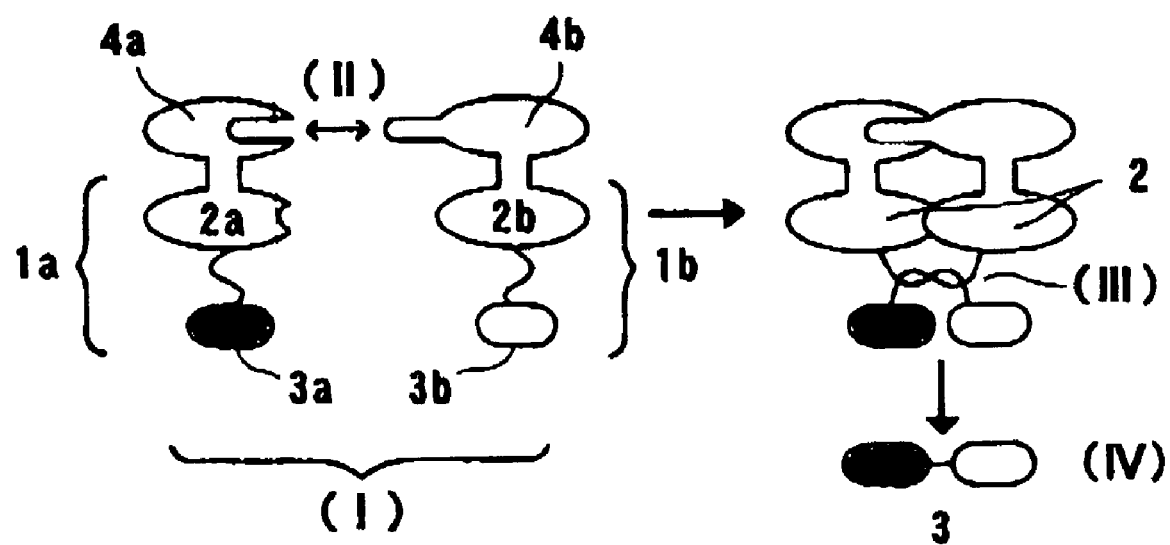
FIG. 1 is a schematic drawing illustrating an example of the structure and operation principle of the probe for protein—protein interaction analysis of the present invention. Here, (I) illustrates co-presence of protein pairs and probes; (II) illustrates protein—protein interaction; (III) illustrates protein splicing; and (IV) illustrates indicator protein linkage. Furthermore, (1a) denotes the probe "a" for protein—protein interaction analysis; (1b) denotes the probe "b" for protein—protein interaction analysis; (2a) denotes the N-terminal polypeptide of an intein; (2b) denotes the C-terminal polypeptide of the intein; and (3) denotes a labeled protein. In particular, (3a) denotes the N-terminal polypeptide of the labeled protein; and (3b) denotes the C-terminal polypeptide of the labeled protein. (4a) denotes protein (or a protein site) A; and (4b) denotes protein (or protein site) B.
Figure 4:
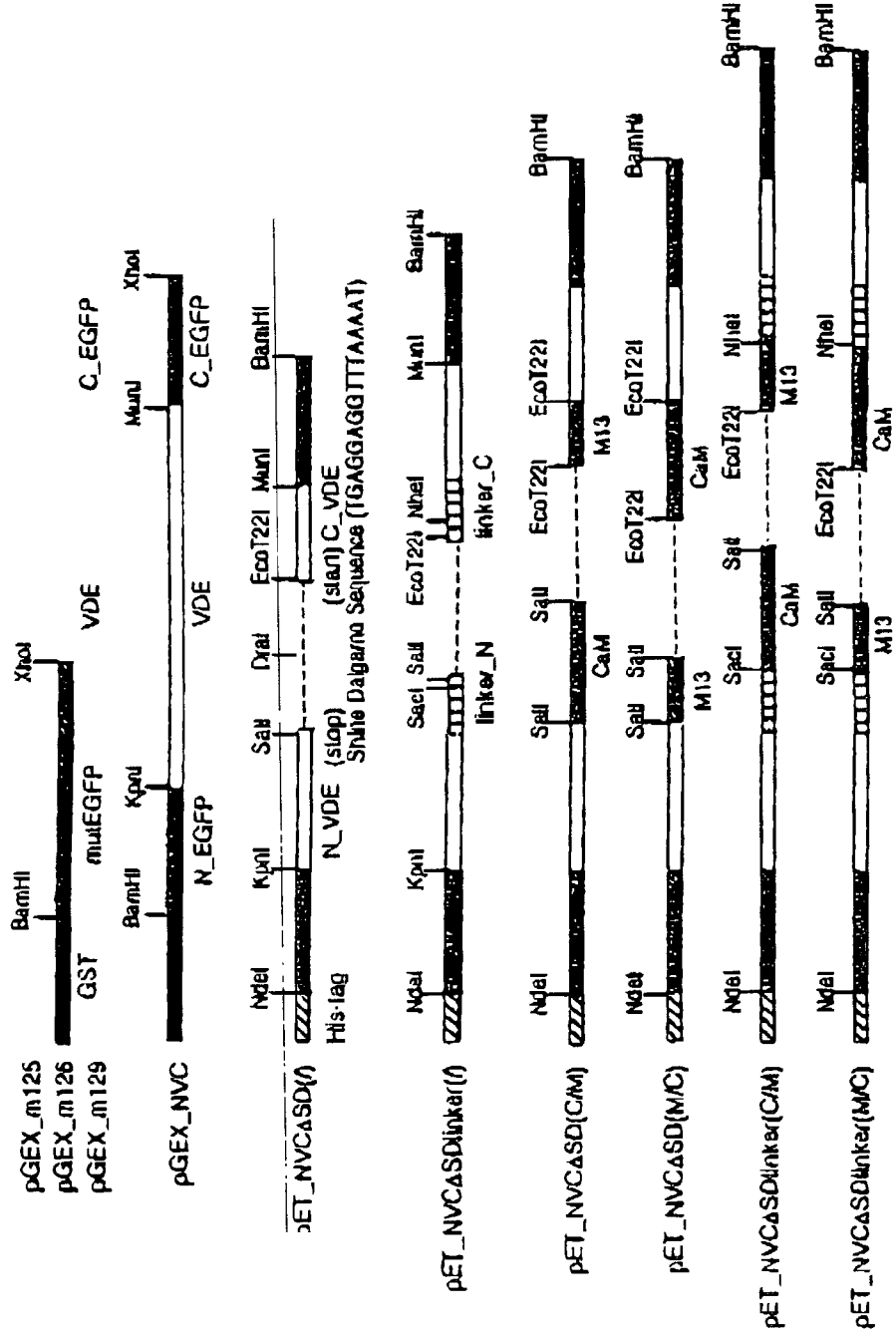
FIG. 4 is a schematic representation of the structure of a plasmid (probe <1> for protein—protein interaction analysis) constructed in the Example of the present invention. Here, the restriction endonuclease splicing sites are shown above the dotted lines indicate the endonuclease domain in the VDE intein, the open bars indicate the VDE intein with no endonuclease, the black bars indicate GST labeling, and the hatching indicates His labeling. Furthermore, the lattice patterns indicate a linker, "stop" indicates a translation termination codon, and "start" indicates a translation initiation codon.

In other words, the probe for protein—protein interaction analysis of the present invention consists of two probes "a" and "b", each probe being connected to a respective protein. FIG. 1 is a schematic representation of the principle of the probe for protein—protein interaction analysis of the present invention.

Of the two probes "a" (1a) and "b" (1b), probe "a" (1a) comprises the N-terminal polypeptide of an intein (2a) and the N-terminal polypeptide of a indicator protein (3a), and probe "b" (1b) comprises the C-terminal polypeptide of the intein (2b) and the C-terminal polypeptide of the indicator protein(3b).

The two probes "a" (1a) and "b" (1b) are linked to the respective proteins A (4a) and B (4b), to analyze the protein A–protein B interaction. Hence, when protein A (4a) and protein B (4b) linked to probe "a" (1a) and probe "b" (1b) are co-present (I) and when the two proteins (4a, 4b) interact with each other (II), the intein (2) is excised through splicing (III). As a result, the indicator protein sites (3a, 3b) bonding to the intein (2) are ligated (IV). Therefore, if the obtained indicator protein (3) is analyzed, the protein—protein interaction can be confirmed.

In this process, if protein A (4a) does not interact with protein B (4b), excision of intein (III) and splicing of exteins do not occur; therefore, the indicator protein (3) is not regenerated (IV) and cannot be detected.

For the probe for protein—protein interaction analysis of the present invention, probes "a" and "b" (1a and 1b) may each be composed only of the intein polypeptide and the indicator protein polypeptide, but may also additionally contain a linker sequence or the like. Accordingly, in probes "a" and "b" (1a and 1b), the intein polypeptides (2a, 2b) and the indicator protein polypeptides (3a, 3b) may be directly bound to each other, or may be bound via a polypeptide such as a linker sequence.

Well-known inteins derived from various organisms can be employed as the intein. Suitable examples include those derived from eukaryotes such as *Saccharomyces cerevisiae* (yeast) Sce VMA, *Candida tropiallis* (*Candida* fungi) Ctr VMA; those derived from eubacteria such as *Mycobacterium tuberculosis* (tubercle *bacillus*) Mtu recA; and those derived from paleobacteria such as *Thermoplasma asidophilum* Tac VMA. In addition, *Cyanobacterium synechocystis* sp. (*cyanobacterium*) DnaE may also serve as the intein.

When protein A (4a) interacts with protein B (4b) in the probes (1a, 1b) for protein—protein interaction analysis of the present invention, the inteins are preferably site-specific endonucleases to provide for autocatalytic intein excision.

Specifically, intein derived from yeast VMA and Ssp DnaE intein derived from *cyanobacterium* are the preferred examples. In yeast VMA, the nascent translation product, 120-kDa VMA1, catalyzes protein splicing to give a 70-kDa $H^+$-ATPase sub-unit and a 50-kDa site-specific endonuclease (VDE, or PI-SceI). This VDE is preferably used as the intein sites (2a, 2b) in the probes (1a, 1b) for protein—protein interaction analysis. For the Ssp DnaE derived from *cyanobacterium*, the DNA sequence of the strain PCC6803 has been clarified (the N-terminal has 123 amino acid residues and the C-terminal has 36 amino acid residues); moreover, it is a natural split intein, and ligation of N- and C-extein is known to occur therein (Wu, H., Hu, Z., Liu, X., XU., M., Q., *Proc. Natl. Acad. Sci. USA* 1998, 95, 9226–9231). Therefore, Ssp DnaE intein is easy to handle, and preferred as the intein sites (2a, 2b) in the probes (1a, 1b) for protein—protein interaction analysis.

Of the various inteins mentioned above, the *cyanobacterium*-derived Ssp DnaE intein is preferred, because the protein—protein interactions in mammal cells can also be detected with high sensitivity. Needless to say, other known or novel inteins may also be employed.

For effective excisions of intein and splicing (III) (1a, 1b) of the present invention, probes 1a and 1b for protein—protein interaction analysis have to be correctly folded and sites have to be correctly aligned, so that the two sites participating in protein splicing be adjacent to each other (Duan, X., Gimble, F. S. and Quiocho, F. A., *Cell* 1997, 89, 555–564). Accordingly, the inteins derived from organisms may be directly used or they may be designed so as to facilitate the splicing, for example, by transforming or deleting some of the amino acid residues, or by introducing a suitable linker sequence.

For example, for the above-mentioned VDE, a mutant obtained by deleting the endonuclease domain and substituting with a flexible dodecapeptide linker is known to demonstrate a high splicing activity (Cooper, A. A., Chen, Y. J., Lindorfer, M. A., Stevens, T. H., *EMBO J.* 1993, 12, 2575–2583; Chong, S., Xu, M.-Q., *J. Biol. Chem.* 1997, 272, 15587–15590). On the other hand, the *cyanobacterium*-derived Ssp DnaE is a naturally split intein, as mentioned above, and is known to fold correctly and splice the exteins. The above-mentioned linker sequence may or may not be introduced into dnaE.

The above-described intein is split into the N-terminal polypeptide (2a) and the C-terminal polypeptide (2b). In the probes (1a, 1b) for protein—protein interaction analysis of the present invention, the split polypeptides (2a, 2b) are bound to the N-terminal polypeptide (3a) of a indicator protein and the C-terminal polypeptide (3b), respectively, to become a probe.

On the other hand, in the probes (1a, 1b) for protein—protein interaction analysis of the present invention, the indicator protein sites are directly peptide bonded and linked (IV) when the intein is spliced out and probes "a" and "b" (1a, 1b)(III) are spliced by the interaction(II) of proteins A and B. The indicator protein (3) may be any protein that can be analyzed again by the linkage (IV). For example, fluorescent protein and emission-catalyzing enzyme are preferably employed. Fluorescent proteins such as green fluorescent protein (GFP) are preferred because they emit light after protein linkage and can be analyzed visually. Emission-catalyzing enzymes such as luciferase are also preferred because they form active centers after linkage and emit light that can be easily detected with a luminometer. For the split N- and C-terminals of luciferase to give individually no fluorescence and to restore the activity again after bonding, the luciferase must be split so that its active center is divided into two. The luciferase enzyme is known to be folded into two domains that sandwich a broad comprising an active center, one being a large N-terminal domain comprising one β-barrel and two β-sheets and the other is a C-terminal site (Waud, J. P., Sala-Newby, G. B., Matthews, S. B., Campbell, A. K., *Biochim. Biophys. Acta* 1996, 1292, 89–98; Conti. E. Franks, N. P., Brick, P., *Structure* 1996, 4, 287–298). Accordingly, it is preferred that the enzyme luciferase be split into 3a and 3b at the flexible site where the two domains are linked. With respect to the luciferase enzyme, it is also known that the N-terminal polypeptide (3a) has a cysteine (Cys) residue in the bonding site with the N-terminal polypeptide(2a) of the intein, has a tyrosine (Tyr) residue upstream of −1 position thereof, and has alanine (Ala) and phenylalanine (Phe) in the −3 and −4 positions, respectively, thereby enabling even more efficient splicing. Therefore, effective splicing may be induced by producing a mutant (R437C) in which the 437th arginine residue is converted into cysteine, a mutant (D436Y) in which the 436th aspargic acid residue is converted into tyrosine, and a mutant (I434A) in which the 434th isoleucine residue is converted into alanine.

As mentioned hereinabove, the invention of this application provides the probe for protein—protein interaction analysis. Furthermore, one probe (e.g., probe "a") is linked to one protein (protein A) whose interaction is to be confirmed, the other probe (probe "b") is linked to the other protein (protein B) whose interaction is to be confirmed, and the two probes are made to coexist in a close proximity, thereby enabling the analysis of interaction between proteins A and B based on the above-mentioned principle and mechanism.

The proteins (4a, 4b) may be linked with the probes (1a, 1b) by any method, as long as the proteins and the probes are not affected. For example, any ordinary chemical, biochemical or genetic engineering techniques can be employed.

Any method may be employed for detecting and analyzing protein—protein interactions (light emission) by using the probe for protein—protein interaction analysis of the invention. Experimental methods and detectors generally used in the field of chemistry and biochemistry may be employed. For example, detection and analysis can be easily conducted by using a luminometer.

Embodiments of the invention are described in more detail in the following Examples with reference to the drawings attached. It goes without saying that the invention is not limited to these Examples, and various changes and modifications may be made.

EXAMPLES

Example 1

Construction of Probe <1> for Protein—Protein Interaction Analysis

A yeast VMA1-derived intein (VDE) was used as the intein site of probe <1> for protein—protein interaction analysis.

Of the 454 amino acids constituting VDE, Cys1 is taken as the first amino acid residue and Asn454 is taken as the last amino acid residue. The C-extein starts from Cys455, and the extein residue adjacent to Cys1 is numbered −1. The numbers then increase as −2, −3, . . . toward the N_Extein.

For the labeled site, a green fluorescent protein derived from light-emitting jelly fish (*Aequorea victoria*) (EGFP, described, for example, in *Current Biology* 1996, 6 (2), 178–182) was used.

In probe <1> for protein—protein interaction, one Cys residue, a Gly residue upstream of the −1 position, and three hydrophobic amino acid residues at −5, −4 and −3 positions have to be present in the N-terminal polypeptide of EGFP as the joining sections for splicing.

Accordingly, the amino acid residues between 1124 and 1129 where the N-terminal polypeptide structure of EGFP is relatively stable were substituted as follows (FIG. 2).

(1) Mutation of I129C and E125I of EGFP was conducted. The mutants showed fluorescence, and excitation and emission peaks were observed at 488 nm and 510 nm identical to those of EGFP.

(2) Fluorescence disappeared with L126Y mutation at m125 although the expression level of the mutant was the same.

The results indicated that the m129EGFP mutant was folded incorrectly and/or splicing sites of the fluorescent protein sites could not be linked due to L126Y mutation.

Accordingly, a m125EGFP mutant for which I129C and E125I mutation was performed was used as the indicator protein site of the probe for protein—protein interaction. This indicator protein site is hereinafter referred to as an EGFP mutant.

Example 2

Confirmation of Splicing in Single Polypeptide

To confirm whether protein splicing occurred in a single polypeptide in which VDE was sandwiched between the N-terminal polypeptide and C-terminal polypeptide of the EGFP mutant, pGEX-NVC was expressed at 25° C. in *E. coli*.

(1) Cells of *E. coli* DH5α were used to express a glutathion S-transferase fused protein(GST). A plasmid that covers the VDE region and the N- and C-terminal polypeptides of the EGFP mutant was fused to the GST gene under control or a tac promoter. This produced a chimera protein comprising GST (26 kDa), 125 residues (13 kDa) from the N-terminal polypeptide of the EGFP mutant, VDE (50 kDa) and the C-terminal polypeptide (14 kDa) of the mutant.

(2) The protein obtained was extracted from the *E. coli* cells, purified, and identified by SDS-PAGE. The indicator protein and 10 to 225-kDa marker (Novagen) were added and electrophoresis was conducted on a 12 to 15% SDS-PAGE gel. The gel was visualized by Coomassie Brilliant Blue staining.

Western blotting was conducted by using anti-VDE polyclonal antibody, anti-His-labeled polyclonal antibody (Santa Crus Biotechnology), or anti-GFP monoclonal antibody (BioRad) as the probe.

All the enzymes necessary for cloning were obtained from Takara Biomedical and used according to the manufacturer's instructions manual.

The PCR fragments were sequenced using a genetic analyzer, ABI310.

The main component of the crude product was a protein of about 50-kDa (FIG. 3b). It matched the size of the extein linked to VDE (50-kDa) and GST. In other words, this component was assumed to be a fused protein of GST and the N-terminal polypeptide of the EGFP mutant (26-kDa+13-kDa).

From this result, it was found that the 103-kDa precursor of the fused protein was split into the 50-kDa VDE and the 53-kDa GST-EGFP mutant fused protein.

In addition, the molecular weights of VDE and GST-EGFP mutant fused protein were evaluated by Western blotting.

The anti-VDE and anti-GFP antibodies were specifically reacted with the excised 50-kDa intein (FIG. 3d) and the 53-kDa GST-EGFP mutant fused protein (FIG. 3e), respectively. The components observed in the vicinity of 100-kDa of the unspliced precursor were analyzed using these antibodies.

The GST-EGFP mutant fused protein was further identified with a GST-affinity column. When the crude product was passed through an affinity column and the proteins bound to the resin were taken out using PreScission protease and then subjected to SDS-PAGE (FIG. 3c), a band was observed at 25-kDa. This result almost matches the molecular weight of the EGFP mutant.

(3) The fluorescent spectrum of the protein purified with the affinity column was then measured. The maximum wavelength of excitation and emission was 488 nm and 510 nm, respectively, those results matching the values for EGFP.

The above results indicated that the VDE located in the center of the single polypeptide was excised by splicing, the N- and C-terminal polypeptides of the EGFP mutant were linked by peptide bonding, and the obtained EGFP mutant folded correctly to form a fluorophore.

Example 3

Effectiveness of Probe <1> for Protein—Protein Interaction Analysis (1) A recombinant fused protein labeled with His at its N-terminal was obtained by using cells of *E. coli* BL21 (DE3).

In order to test protein—protein interaction, GST of pGEX_NVC was substituted with the His-label of a pET16-b vector, and the splicing functional site was split to obtain pET_NVCΔSD(/).

The splitting was realized by substituting the functionally unnecessary endonuclease motif that exists in the 185th to 389th amino acid region of the mutant with a cassette consisting of ((translation termination codon)—(Shine-Dalgarno sequence)—(translation initiation codon)).

The resulting plasmid pET_NVCΔSD(/) was a two-gene operon essentially composed of gene 1 that encodes the N-terminal polypeptide of EGFP and VDE (N_EGFP-VDE) and gene 2 that encodes the C-terminal polypeptide of VDE and EGFP (C_VDE-EGFP).

In order to bring the N- and C-terminal polypeptides of VDE spatially close to each other during protein—protein interaction, a bendable peptide linker having repetitive Gly-Asn sequences was introduced between the translation termination codon and the translation initiation codon (pet_NVCΔSD linker (/)).

In order to confirm the presence of specific protein—protein interaction that facilitates the splicing phenomenon providing EGFP in *E. coli*, calmodulin (CaM) and its target peptide M13 were selected as model proteins.

CaM and M13 are preferred, because the structures thereof have been clarified by NMR (Ikura, M., et al., *Science* 1992, 256, 632–638) and, therefore, the distance between any amino acid in CaM and any amino acid in M13 is known.

(2) The recombinant plasmids pET_NVCΔSD(C/M), pET_NVCΔSD linker (C/M) and pET_NVCΔSD linker (/) were introduced into the cells of *E. coli* to obtain the corresponding fused protein.

In order to induce the intracellular splicing, the protein expression was effected for 12 hours at 25° C. and the cells were thereafter stored for 1 or 2 days at 4° C.

Gene 1 protein expression was confirmed by an anti-His labeled antibody (FIG. 5A). The main components analyzed by the antibody were proteins of 55-kDa (FIG. 5A a, d), and their size was about the same as that of the unspliced precursor of N_EGFP-VDE(36-kDa) with CAM (17-kDa) or its linker (1-kDa).

When a lysate of *E. coli* having a pET_NVCΔSD linker (/) plasmid was subjected to SDS-PAGE as a control, a single band of N_EGFP-VDE (FIG. 5A, f) was obtained.

The expression level of the unspliced precursor proteins obtained from these three plasmids was almost the same.

On the other hand, the gene 2 protein product was identified by an anti-GFP monoclonal antibody, and was found to be the C-terminal polypeptide of EGFP.

In addition, in the cell that expressed pET_NVCΔSD(C/M) and pET_NVCΔSD linker (C/M), the size of the expression protein obtained from the gene operon well agreed with that of the precursor protein of N_VDE-EGFP (20-kDa) with M13 (3-kDa) (FIG. 5B, a) or the linker-containing M13 (4-kDa) (FIG. 5B, d). Similarly, the control plasmid expressed the expected protein (FIG. 5B, f). The expression levels of all three proteins obtained from operon II were the same.

Figure 6:
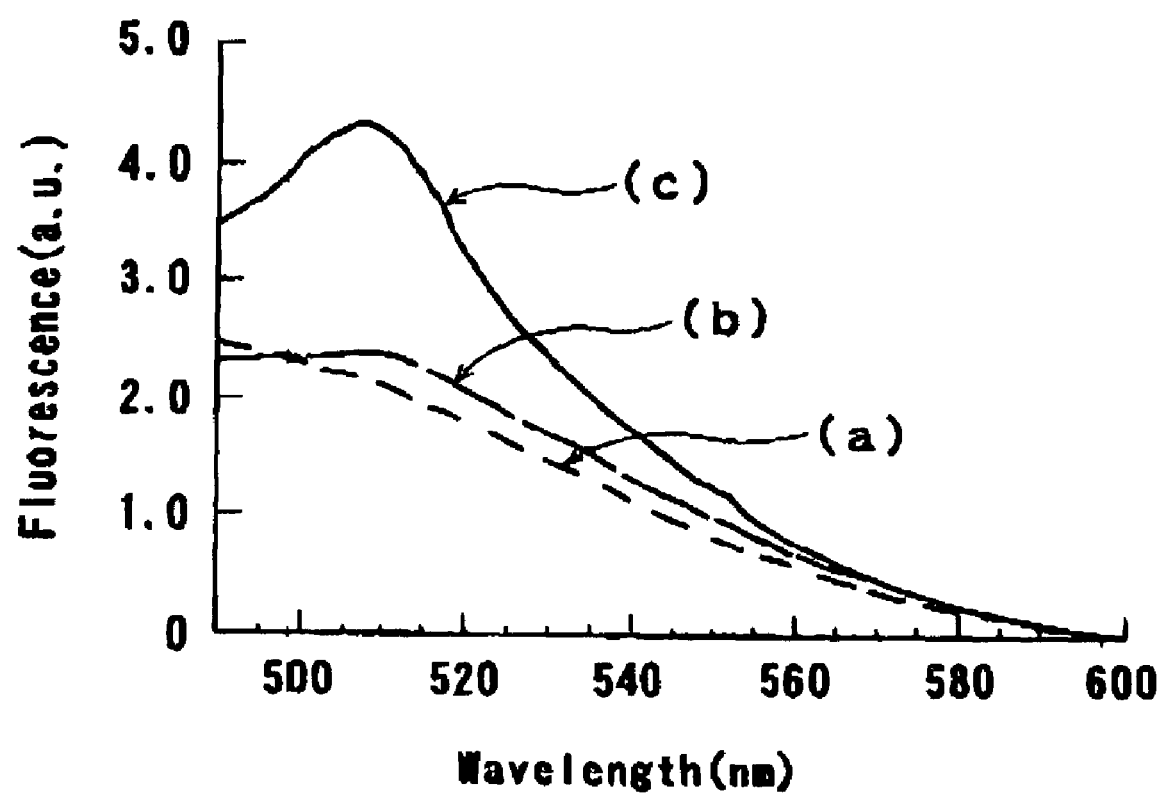
FIG. 6 shows the fluorescence spectra of crude products from E. coli having plasmids (probe <1> for protein—protein interaction analysis) constructed in the Example of the present invention (excitation: 470 nm, band width: 5.0 nm; and the emission band width: 5.0 nm). (a) indicates NVCΔSD linker (/); (b) indicates NVCΔSD (C/M); and (c) indicates NVCΔSD linker (C/M)

FIG. 6 shows the flourescence spectra of lysates of *E. coli* cells, each carrying one of the above-mentioned plasmids. For the cells of *E. coli* comprising pET_NVCΔSD linker (/), no spectral change was observed. From the cells of *E. coli* having pET_NVCΔSD(C/M) and having co-expressed CaM and M13, a certain change in fluorescence emission at 510 nm was observed. On the other hand, in the co-expression of CaM and M13 where a bendable peptide linker was bonded to N_EGFP-VDE and C-VDE-EGFP, fluorescence at 510 nm changed significantly. The fluorescence intensity of the crude product from the cells of *E. coli* that had pET_NVCΔSD linker (C/M) was sufficient to differentiate those cells from the cells that carry the control plasmid pET_NVCΔSD linker (/) or the plasmid not encoding the foldable bendable linker pET_NVCΔSD linker (C/M).

These results indicated that the CaM-M13 interaction resulted in trans splicing and ligation of N- and C-terminal polypeptides of the EGFP mutant that formed the EGFP fluorophore.

Example 4

Effect of Linker in Probe <1> for Protein—Protein Interaction Analysis

To induce splicing, it is necessary that the N- and C-terminals of VDE be correctly folded. Such correct folding is attained only when the C-terminal N_VDE is close to the N-terminal C-VDE.

Regarding CaM and M13, the distance between the N-terminal of CaM and the C-terminal of M13 is 50 Å (from Brookhaven Protein Data Bank). This distance can be too large for N_VDE to be close to C-VDE and, therefore, was thought to inhibit the correct folding in *E. coli* having the plasmid pET_NVCΔSD linker (C/M).

However, actually, a clear increase in the fluorescence intensity at 510 nm was observed in plasmid pET_NVCΔSD linker (C/M), the 10- and 9-amino acid linkers that were linked to the N_ and C_VDEs, respectively, provided bendability necessary for the VDE folding, and the conformation for effective VDE splicing was attained.

Example 5

Construction of Probe <2> for Protein—Protein Interaction Analysis

A plasmid was constructed as described below by using *E. coli* strain DH5α as a host.

DnaE derived from *cyanobacterium Synechocystis* sp. PCC6803 was used as the intein site for a probe <2> for protein—protein interaction analysis. As the indicator protein for the probe, a wild firefly-derived luciferase (Lum-F) (pLucAll) was split between the 437th amino acid and the 438th amino acid and used as N-terminal (pLucN) and C-terminal (pLucC).

Figure 7:
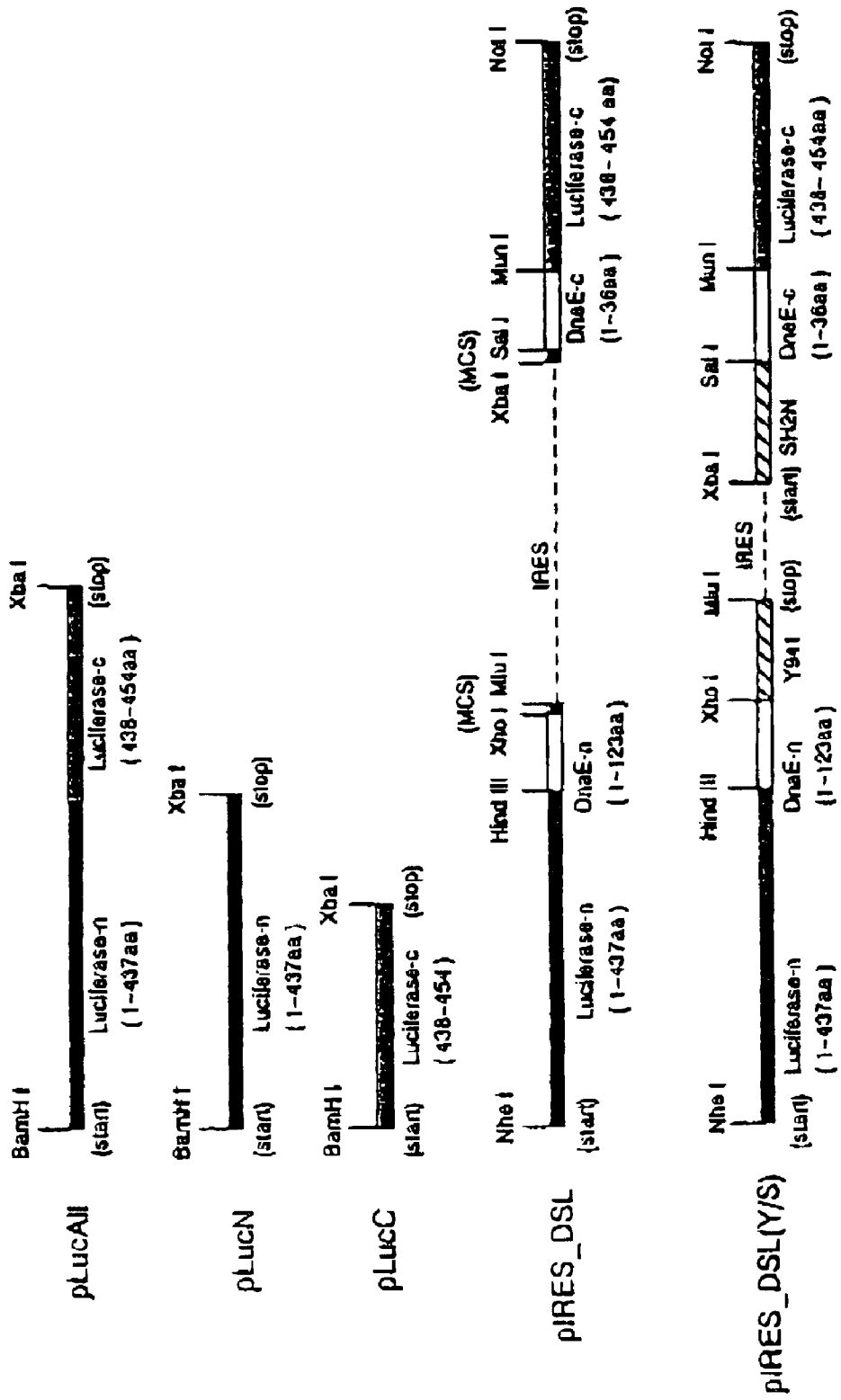
FIG. 7 shows the structure of a plasmid used in the Example of the present invention. Here, the dotted lines indicate an intracellular ribosome entry site (IRES); the cDNAs of pLucAll, pLucN and pLucC are inserted into pcDNA3.1 (+); "Stop" and "Start" indicate translation termination and initiation codons, respectively.

FIG. 7 shows the structure of the luciferase and luciferase segments.

(1) Splitting of Luciferase

First, the absence of enzymatic activity in pLucN and pLucC was confirmed by transitionally expressing the two luciferase segments in human insulin receptor-overexpressing Chinese hamster ovarian cells (CHO-HIR).

Thus, the CHO-HIR cells were transfected with 1 μg of each plasmid (pLucAll, pLucN, and pLucC) together with 0.01 μg of a control plasmid (pRL-TK), and incubated in a 12-well plate for 45 hours. After the incubation, the emission was measured with a luminometer.

As a control, the CHO-HIR cells containing no plasmid were incubated under the same conditions.

In order to correct the transfection efficiency error in each well of the plate, a dual-luciferase assay using a *Renilla*-derived luciferase (Lum-R) was conducted and the transfection efficiency in each well was corrected.

Figure 8:
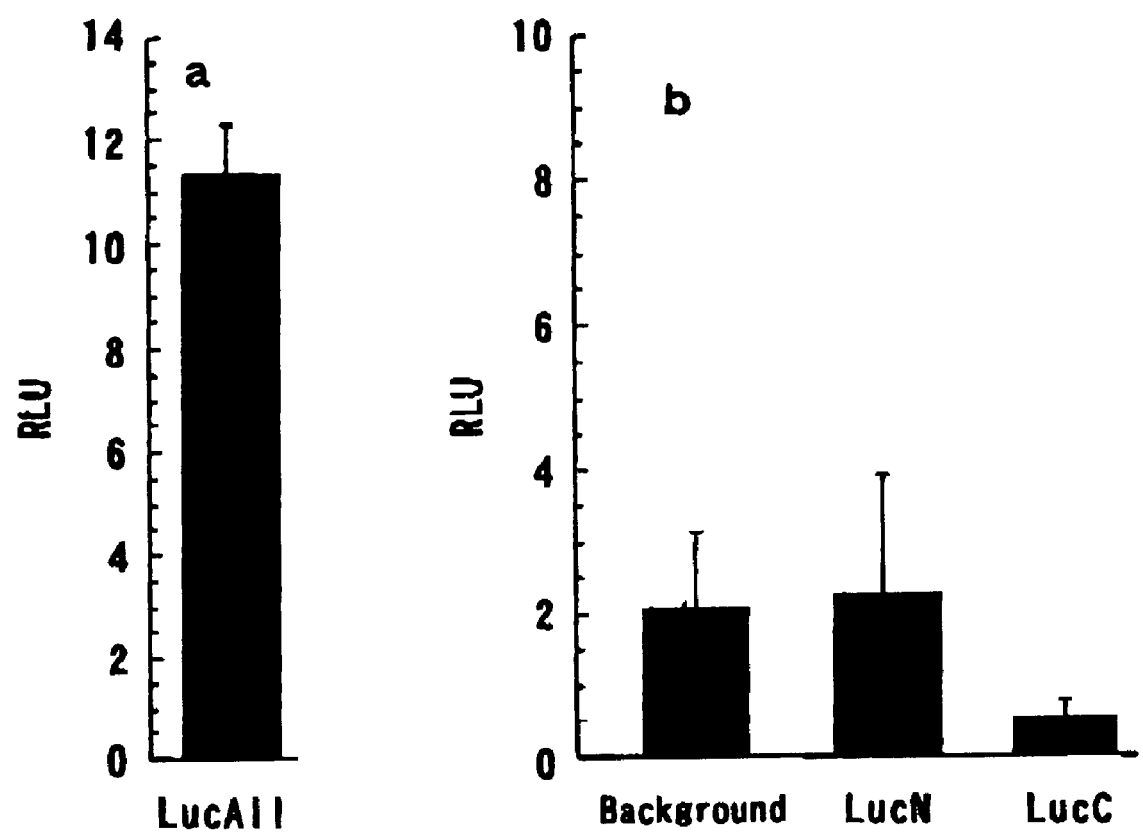
FIG. 8 shows the emission intensity of LucN alone, LucC alone and LucAll in the Example of this invention.

FIG. 8 shows the relative emission intensity (RLU) of each luciferase (or each luciferase segment).

The RLU of the CHO-HIR cells where the wild firefly luciferase (LucAll) was expressed was 11.4 (FIG. 8a) but the RLU of the CHO-HIR cells where only LucN or LucC was expressed was $2.2 \times 10^{-4}$ and $4.5 \times 10^{-5}$, respectively (FIG. 8b). Furthermore, the RLU (background) of the CHO-HIR cells transfected with Lum-R itself was $2.2 \times L\ 10^{-4}$ indicated that LucN or LucC alone showed no emission activity.

(2) Splitting of DnaE

As mentioned above, *Synechocystis* sp. PCC6803-derived DnaE was split into N-terminal segment of 123 amino acid residues and C-terminal 36 amino acid residues.

(3) Probe <2> for Protein—Protein Interaction

The above-described N-terminal of DnaE in (2) was ligated with LucN in (1), the C-terminal of DnaE in (2) was ligated with LucC in (1), and then they were inserted into a multicloning site (MCS) of pIRES (Invitrogen), which is a bicistronic expression vector, to obtain pIRES-DSL. The resulting plasmid (pIRES-DSL) had two MCSs: at the 3'-terminal of the N-terminal DnaE and at the 5'-terminal of the C-terminal DnaE (MCS-A and MCS-B, respectively). Proteins or protein domains which interact with each other or which are to be tested for their interaction can be introduced into those MCSs.

FIG. 7 shows the structure of pIRES-DSL.

Example 6

Effectiveness 1 of Probe <2> for Protein—Protein Interaction Analysis (1) In order to confirm that probe <2> for protein—protein interaction analysis constructed in Example 5 acts effectively and induces splicing of luciferase, an oligopeptide (Y941) that comprises the 941st tyrosine residue of IRS-1 (which is known to participate physiologically in insulin signal transduction) and SH2N domain derived from phosphatidylinositol 3-kinase, which is a target protein thereof, were used (White, M. F., *Diabetologia* 1997, 40, S2–S17).

A plasmid PIRES-DSL (Y/S) with Y941 inserted into MCS-A and SH2N inserted into MCS-B and a pRL-TK vector were transiently coexpressed in CHO-HIR cells.

FIG. 7 shows the structure of the pIRES-DSL (Y/S).

First, CHO-HIR cells were transfected with 2 μg of the plasmid (pIRES-DSL (Y/S)) and 0.02 μg of the control plasmid pRL-TK in a 6-well plate. The cells were incubated for 45 hours, and then the culture was substituted with an FBS-free solution of $1.0 \times 10^{-7}$ M human insulin and the CHO-HIR cells were stimulated through incubation (at 37° C.) for 72 hours, 3 hours or 5 minutes. The insulin solution of the cells incubated for 5 minutes was then incubated for 175 minutes in an FCS-free culture containing no insulin.

Figure 9:
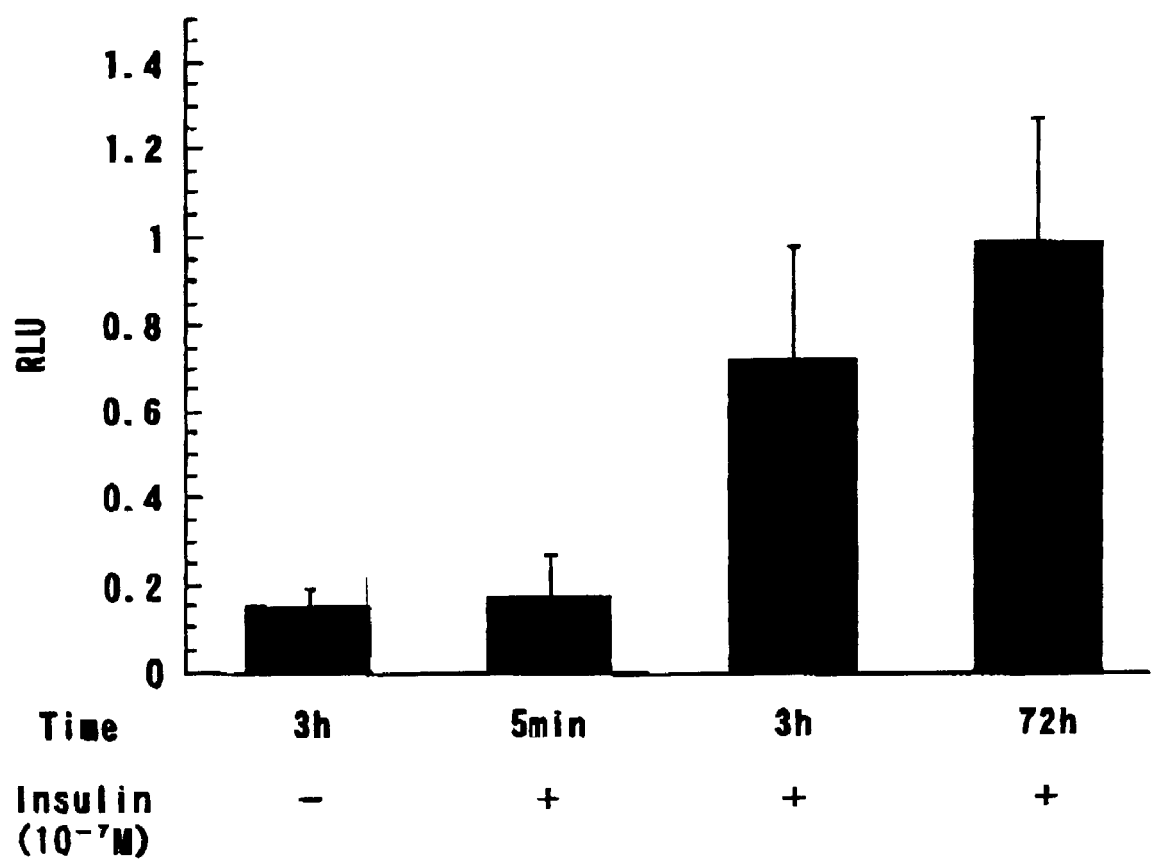
FIG. 9 shows the enhancement of protein splicing by insulin in the Example of this invention.

FIG. 9 shows the emission intensity, which is represented by RLU, after the insulin stimulation.

The corrected luciferase activity of the CHO-HIR cells stimulated with insulin for 72 hours, 3 hours and 5 minutes was 1.0, 0.73, and 0.18, respectively. The emission intensity (background) of the cells incubated in the insulin-free culture was 0.15, and was found to be almost the same as that of the cells stimulated with insulin for 5 minutes.

Furthermore, the emission intensity, which was represented by RLU, of the cells stimulated with insulin for 3 hours or longer was found to be more than 4 times that of the background value. The kinase activity of the cells observed herein resulted from the specific interaction between SH2N and the peptide Y941 (the 941st amino acid of which is tyrosine) phosphorylated with an insulin receptor. This in-trans folding and splicing of DnaE occurred effectively in probe <2>, for protein—protein interaction, LucN and LucC were linked, and luciferase emission was reproduced.

An Y941 mutant, in which the tyrosine residue in Y941 was substituted with an alanine residue that was not phosphorylated with the insulin receptor, was then constructed and tested in the same manner as described above.

Figure 10:
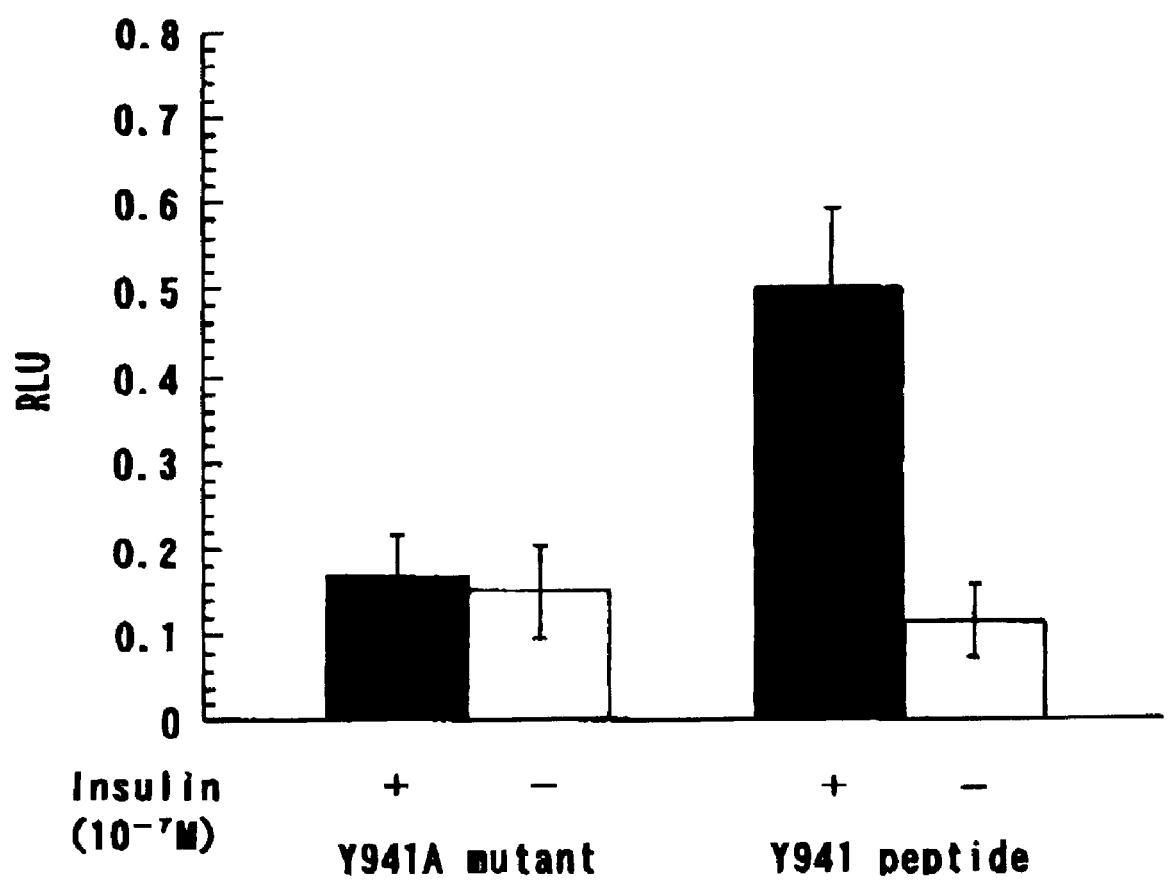
FIG. 10 shows the influence of amino acid mutation in the Example of this invention.

The results are shown in FIG. 10.

In the CHO-HIR cells where the Y941 mutant was expressed, the corrected luciferase emission was on the same level as that of the background. This confirmed that the protein interaction with SH2N was due to phosphorylation of tyrosine in Y941.

Example 7

Effectiveness 2 of Probe <2> for Protein—Protein Interaction Analysis

Quantitative analysis of insulin-induced protein—protein interaction in CHO-HIR cells was conducted by using probe <2> for protein—protein interaction analysis constructed in Example 5.

First the insulin concentration dependence of the RLU value was confirmed. After the CHO-HIR cells were coexpressed by pIRES-DSL (Y/S) and PRL-TK in the same manner as described above, the cells were stimulated at 37° C. for 3 hours with insulin of various concentrations between $1.0 \times 10^{-13}$ and $1.0 \times 10^{-7}$ M by the above-described method.

Figure 11:
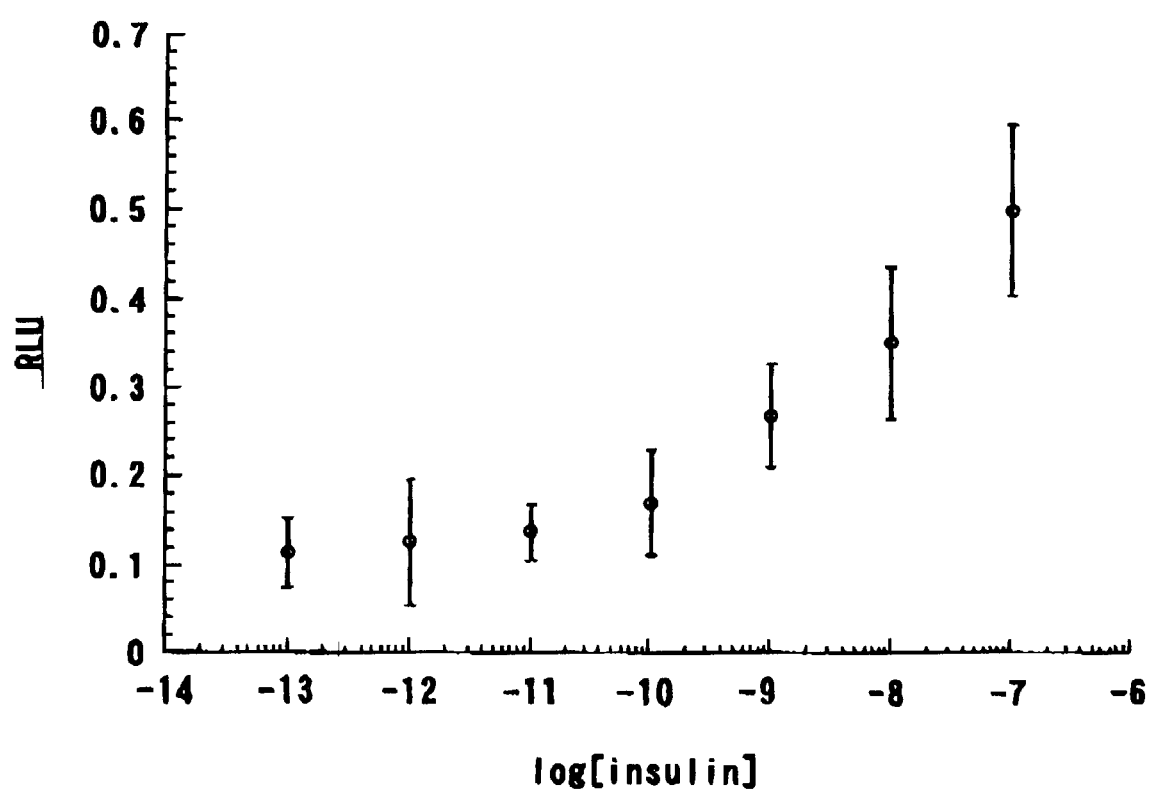
FIG. 11 shows the insulin concentration dependency of Lum_F emission intensity in the Example of this invention.

FIG. 11 shows the RLU.

The emission intensity of the cells was confirmed to increase with insulin concentration.

INDUSTRIAL APPLICABILITY

As described in detail hereinabove, the present invention provides a probe for protein—protein interaction analysis that enables accurate and simple analysis of protein—protein interactions. The invention also provides a method for the analysis of protein—protein interactions using the probe for protein—protein interaction analysis.

The present method for analysis of protein—protein interactions does not require any reporter gene or substrate as in the conventional methods, and enables simple and accurate analysis. Furthermore, protein—protein interactions can be also analyzed with high-sensitivity in mammal cells.

Accordingly, the probe for protein—protein interaction analysis in accordance with the present invention enables fast and simple analysis of the mechanisms of protein—protein interactions in various organisms, such as protein—protein interactions in cell membranes and receptor activation by hormones inside the cells.

The invention claimed is:

1. A set of probes for analyzing protein A–protein B interactions, which set comprises:
   (i) probe "a" comprising a fusion polypeptide wherein the carboxyl terminus of an N-terminal portion of an indicator protein is fused to the N-terminus of the N-terminal portion of an intein polypeptide, and wherein the C-terminus of the intein polypeptide is fused to a target protein A; and
   (ii) probe "b" comprising a fusion polypeptide wherein the amino terminus of a C-terminal portion of the indicator protein is fused to the C-terminus of the C-terminal portion of the intein polypeptide, and wherein the N-terminus of the intein polypeptide is fused to a target protein B, wherein the N-terminal portion of the intein and the C-terminal portion of the intein are sufficient to effect trans-splicing, and wherein the N-terminal portion of the indicator protein and the C-terminal portion of the indicator protein constitute a functioning indicator protein after intein mediated trans-splicing occurs.

2. The set of probes according to claim 1 wherein the indicator protein is a green-fluorescent protein or a luminescent enzyme.

3. The set of probes for analyzing protein A–protein B interaction of claim 2 wherein the luminescent enzyme is a luciferase.

4. The set of probes for analyzing protein A–protein B interaction of claim 1, wherein the C-terminus of the intein polypeptide of probe "a" and the N-terminus of the intein polypeptide of probe "b" each further comprise a peptide linker sequence.

5. A method for analyzing protein A–protein B interaction by using the set of probes of claim 1, which method comprises:
   (i) preparing a recombinant polynucleotide encoding the fused protein of probe "a" under the control of a promoter,
   (ii) preparing a recombinant polynucleotide encoding the fused protein of probe "b" under the control of a promoter
   (iii) transforming an eukaryotic host cell with the recombinant polynucleotides of (1) and (2) and culturing the cell under conditions permitting the expression of the fused proteins encoded by (i) and (ii), so that intein-mediated trans-splicing may occur, and
   (iv) detecting the interaction of protein A with protein B by measuring a change of a signal from the indicator protein resulting from intein-mediated trans-splicing and that consists of the N-terminus of the indicator protein and the C-terminus of the indicator protein,
   whereby the interaction of protein A and protein B is analyzed.

6. A vector for expressing a set of probes for analyzing protein A–protein B interaction, which vector co-expresses two probes wherein probe "a" is a fusion polypeptide comprising an N-terminal portion of an intein polypeptide and an N-terminal portion of an indicator protein, and probe "b" is a fusion polypeptide comprising a C-terminal portion of the intein polypeptide and a C-terminal portion of the indicator protein, wherein the vector comprises:
   (1) a polynucleotide encoding the fusion polypeptide of probe "a" wherein the coding region for the N-terminal portion of the indicator protein is ligated at the 5' side of the coding region for the N-terminal portion of the intein polypeptide, and a 3' side of the coding region for the N-terminal portion of the intein polypeptide is a cloning site for ligating a polynucleotide encoding protein A; and,
   (ii) a polynucleotide encoding the fusion polypeptide of probe "b" wherein the coding region for the C-terminal portion of the indicator protein is ligated at the 3' side of the region for the C-terminal portion of the intein polypeptide, and a 5' side of the coding region for the C-terminal portion of the intein polypeptide is a cloning site for ligating a polynucleotide encoding protein B;
   wherein the N-terminal portion of the intein and the C-terminal portion of the intein are sufficient to effect trans-splicing, and
   wherein the N-terminal portion of the indicator protein and the C-terminal portion of the indicator protein constitute a functioning indicator protein after intein mediated trans-splicing occurs.

7. The vector of claim 6 wherein the indicator protein is a green-fluorescent protein or a luminescent enzyme.

8. A method for analyzing protein A–protein B interaction by using the expression vector of claim 6, which comprises:
   ligating a polynucleotide encoding protein A into the expression vector at the 3' side of the coding region for the N-terminal portion of the intein polypeptide and ligating a polynucleotide encoding protein B into the expression vector at the 5' side of the coding region for the C-terminal portion of the intein polypeptide;
   (ii) transforming an eukaryotic host cell with the vector of step (1) and expressing probe "a" and probe "b" in the eukaryotic host cell under conditions permitting excision of the intein portions of probes "a" and "b" upon the interaction of proteins A and B; and
   (3) detecting the interaction of protein A with protein B by measuring a change of a signal from the indicator protein that is a fusion protein of the N-terminus of the indicator protein and the C-terminus of the indicator protein,
   whereby the interaction of protein A and protein B is analyzed.

* * * * *